United States Patent [19]

DeLuca et al.

[11] Patent Number: 4,973,584
[45] Date of Patent: Nov. 27, 1990

[54] NOVEL 1α-HYDROXYVITAMIN $D_2$ EPIMER AND DERIVATIVES

[76] Inventors: Hector F. DeLuca, 1809 Hwy. Bb, Deerfield, Wis. 53531; Heinrich K. Schnoes, 1806 Summit Ave., Madison, Wis. 53705; Kato L. Perlman, 1 Chippewa Ct., Madison, Wis. 53711

[21] Appl. No.: 321,254

[22] Filed: Mar. 9, 1989

[51] Int. Cl.[5] .................. A61K 31/59; C07J 15/00; C07J 9/00
[52] U.S. Cl. .................................. 514/167; 552/653; 552/544
[58] Field of Search ............... 260/397.2; 552/653, 552/544; 514/167

[56] References Cited

U.S. PATENT DOCUMENTS

| 3,880,894 | 4/1975 | DeLuca et al. | 260/397.2 |
| 3,907,843 | 9/1975 | DeLuca et al. | 260/397.2 |
| 4,588,528 | 5/1986 | DeLuca et al. | 260/397.2 |
| 4,612,308 | 9/1986 | Baggiolini et al. | 260/397.2 |
| 4,717,721 | 1/1988 | DeLuca et al. | 260/397.2 |
| 4,769,181 | 9/1988 | DeLuca et al. | 260/397.2 |

*Primary Examiner*—Mukund J. Shah
*Assistant Examiner*—E. C. Ward
*Attorney, Agent, or Firm*—Andrus, Sceales, Starke & Sawall

[57] ABSTRACT

The invention provides a new vitamin $D_2$ compound, 1α-hydroxy-24-epi-vitamin $D_2$ and certain hydroxy-protected derivatives thereof. The new compound exhibits a distinctive activity pattern comprising high potency in stimulating intestinal calcium transport and little or no activity in inducing bone calcium mobilization or the differentiation of undifferentiated cells in culture, thereby evincing utility in the treatment of diseases characterized by loss of bone mass.

7 Claims, No Drawings

NOVEL 1α-HYDROXYVITAMIN D₂ EPIMER AND DERIVATIVES

This invention was made in the course of work supported by a grant or award from the Department of Health and Human Services. The Government has certain rights in this invention.

This invention relates to vitamin D₂ compounds, and more specifically to the preparation of the novel (24S)-epimer of 1α-hydroxyvitamin D₂, and certain derivatives thereof.

BACKGROUND

The natural vitamin D-derived hormone, 1α,25-dihydroxy-vitamin D₃, and its 25-deoxy analog, 1α-hydroxyvitamin D₃, both exhibit high activity in vivo, being known as potent stimulators of the intestinal absorption of calcium and the mobilization of calcium from bone and as effective promoters of bone calcification. A very similar activity pattern is shown by 1α,25-dihydroxyvitamin D₂ (U.S. Pat. No. 3,880,894) and its 25-deoxy analog, 1α-hydroxyvitamin D₂ (U.S. Pat. No. 3,907,843). These compounds likewise elicit the full spectrum of vitamin D-type responses such as intestinal calcium transport, bone mineral mobilization and bone calcification response in the 1α-hydroxyvitamin D₂ are characterized by having a C-24 stereochemistry as it occurs in the side chain of ergosterol, i.e. these compounds are defined by the structures shown below, where R represents side chains (a) and (b), respectively:

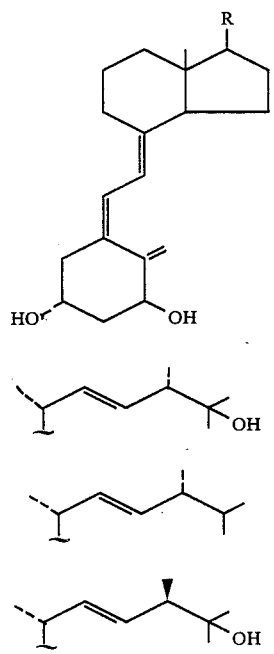

More recently the C-24-epimer of 1α,25-dihydroxyvitamin D₂ has been prepared and tested (U.S. Pat. Nos. 4,588,716 and 4,769,181). This compound is characterized by the structure shown above, where R represents side chain (c). Remarkably, this C-24-epimeric vitamin D derivative exhibits a distinctly different biological activity profile, in that it is active in stimulating intestinal calcium absorption and promoting the calcification of bone, but does not elicit a bone calcium mobilization response.

DISCLOSURE OF INVENTION

This invention provides a new vitamin D analogue, namely 1α-hydroxy-24-epi-vitamin D₂, which may be represented by the structure below, as well as the acyl and alkylsilyl derivatives of that compound.

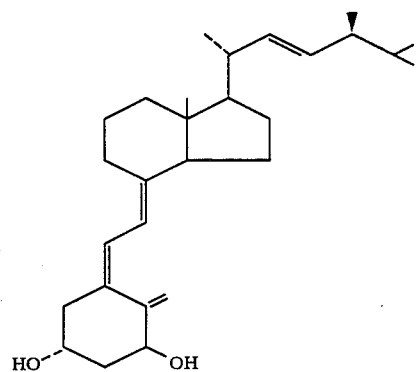

This compound, therefore, is distinguished from the known 1α-hydroxyvitamin D₂, by having the opposite methyl stereochemistry at C-24 (i.e. the 24S configuration), and it is further distinguished by exhibiting a strikingly different pattern of biological activity than the known vitamin D₂ derivative, as more fully described below.

The synthesis of 1α-hydroxy-24-epi-vitamin D₂ requires the construction of an appropriate side chain unit having the desired (S) stereochemistry at the carbon center that is to become carbon-24 in the target compound, and the condensation of that side chain unit with a suitable 1α-hydroxylated vitamin D nucleus so as to generate the desired final product.

The synthesis of the optically active side chain unit comprised the conversion of commercially available, racemic 2,3-dimethylbutanol to the corresponding bromide and then to the magnesium bromide derivative (1) according to published procedures (see T. Suda et al., Chem. Soc. 82, 3396, 1960; Martinez et al., Gazz. Chim. Ital. 97, 96, 1967; Organic Synthesis, Collective volume 2, p. 358, Wiley & Sons, N.Y., 1943).

The magnesium bromide derivative (1) shown below was then reacted with (R)-(+)-p-toluenesulfinic acid (−)-menthyl ester, compound (2) below, under Grignard reaction conditions. This reaction is the key step for it provides a mixture of diastereomeric sulfoxides, namely compounds (3) and (4), which may be readily separated by column chromatography or by high pressure liquid chromatography (hplc) to give both the 2R (compound (3) and the (compound 4) stereoisomers.

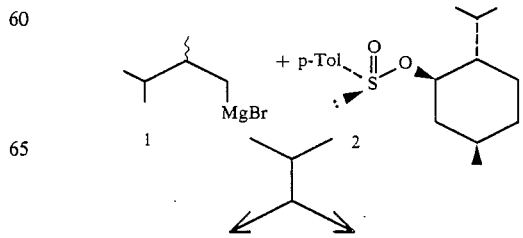

-continued

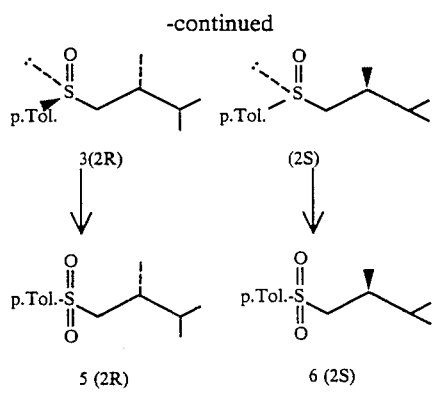

3(2R)  (2S)

5 (2R)  6 (2S)

Subsequent oxidation of p-tolyl-2,3-dimethylbutylsulfoxides 3 and 4 then affords the corresponding optically active sulfones. Thus, as shown in the scheme above, oxidation of sulfoxide (3) with chloroperbenzoic acid gives the (2R)-2,3-dimethylbutyl-p-tolysulfone (5), whereas analogous treatment of sulfoxide (4) gives (2S)-2,3-dimethylbutyl-p-tolysulfone (6).

The preceding reaction sequence provides a novel and efficient method for the preparation of optically active side chain units as their sulfonyl derivatives, which then may be used according to known procedures for the construction of a variety of steroid or vitamin D side chains having a chiral center at C-24. The tolylsulfones (5) and (6) above are new compounds; the corresponding enantiomeric phenylsulfones have been obtained previously by lengthy and elaborate synthesss [Mori et al., Tetrahedron Letters 38, 2099 (1982); Sakakibara et al., Heterocycles 17, 301 (1982); Ferraboschi and Santaniello, Synth. Commun. 14, 1199 (1984); Kocienski et al., J. Chem. Soc. Perkin Trans. 1, 834 (1978)].

For the preparation of the desired 1α-hydroxy-24-epi-vitamin $D_2$ analogue, the (2S)-2,3-dimethyl-p-tolyl-sulfone (6) as obtained by the above procedure is the appropriate side chain unit. Accordingly, compound (6) is reacted with the known 1α-hydroxyvitamin D-22-aldehyde derivative (structure 7, below, where $X^1$ and $X^2$ are hydroxy-protecting groups, e.g. an alkylsilyl group, such as t-butyldimethylsilyl), using the general procedures of Kutner et al., J. Org. Chem. 53, 3450 (1988). This condensation yields the side chain aduct represented by structure (8) below ($X^1$ and $X^2$=hydroxy-protecting group), which is then reduced with a metal amalgam to provide the hydroxy-protected 24-epi-vitamin $D_2$ derivative, structure (9, $X^1$ and $X^2$-hydroxy-protecting groups). Upon removal of the hydroxy-protecting groups according to standard procedures there is obtained the desired 1α-hydroxy-24-epi-vitamin $D_2$ (compound 10, $X^1=X^2=H$).

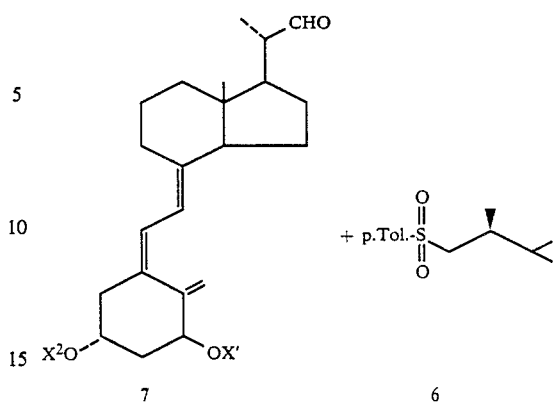

7  6

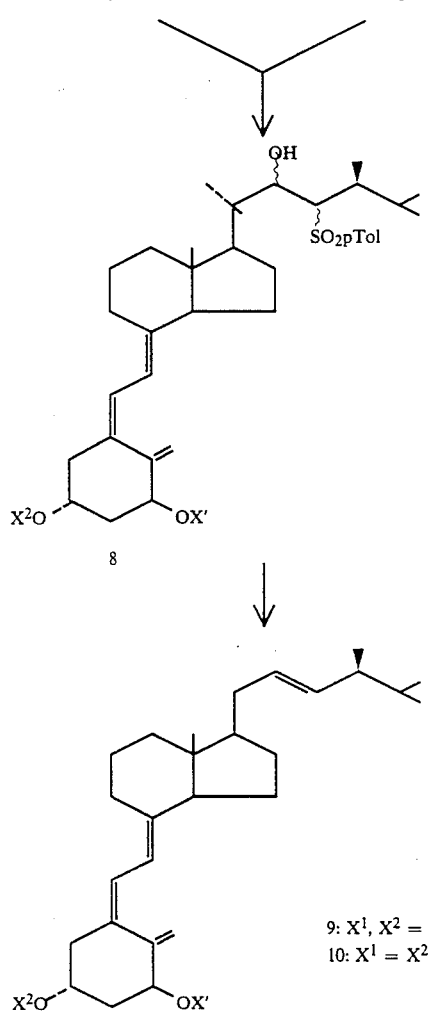

9: $X^1$, $X^2$ = OH-prot. group
10: $X^1 = X^2 = H$

As shown by the above structures, the process of this invention yields both the free hydroxy compound (10), where $X^1$ and $X^2$ are hydrogen, as well as hydroxy-protected derivatives, such as compound (9), where $X^1$ and $X^2$ represent an alkylsilyl group. Furthermore, the hydroxy compound (10) can be converted to other derivatives, by the corresponding 1- and/or 3-acyl derivatives, by standard acylation procedures, to provide the compounds of structure (9), where $X^1$ and $X^2$ represent acyl groups. Alkylsilyl and acyl derivatives of compound (10) find use in applications where enhanced lipid-solubility is desired.

In this specification and the claims, the term 'alkylsilyl' means a trialkylsilicon radical, where each of the alkyl groups may have from 1 to 5 carbons in all isomeric forms. Common examples include trimethylsilyl, triethylsilyl and t-butyldimethylsilyl. The term 'acyl' signifies an aliphatic acyl group (alkanosyl group) from 1 to 5 carbons in all isomeric forms (e.g. formyl, acetyl, propionyl, etc.), or an aromatic acyl group, such as benzoyl, or nitro, halo or methyl substituted benzoyl groups.

The process of this invention is more particularly described by the following illustrative examples. In these examples, designation of products or intermediates by Arabic numerals, e.g. 1, 2, 3, ... etc. refers to the structures so numbered in the preceding description.

EXAMPLE 1

(2R)-2,3-Dimethylbutyl-p-tolylsulfoxide (3) and (2S)-2,3-dimethyl-p-tolylsulfoxide (4)

Magnesium turnings (0.24 g, 10 mmol) and a crystal of $I_2$ were placed in a dry flask and covered with 5.0 mL of anhydrous tetrahydrofuran. 1-Bromo-2,3-dimethylbutane (1.54 g, 8 mmol) was added slowly with stirring under nitrogen atmosphere and occasional cooling. The mixture was stirred at room temperature for 1.5 h or until most of the magnesium was consumed. This mixture (containing compound 1) was cooled and 2.35 g (R)-(+)-p-toluenesulfinic acid (−)-menthyl ester (compound 2) (10 mmol) in 10.0 mL of anhydrous tetrahydrofuran was added. The mixture was stirred under nitrogen atmosphere at room temperature for 16 h, cooled and decomposed with saturated $NH_4Cl$ solution. The organic layer was separated and the squeous phase extracted several times with ether. The combined organic phase was washed with water and brine, dried with $MgSO_4$, filtered and evaporated. The residue was chromatographed on a 70–270 mesh silica gel column to give 1.26 g of diastereomeric sulfoxide mixture. This was separated by flash chromatography on a 230–400 mesh silica gel column with ethyl acetate and hexane mixtures or by semipreparative HPLC (Zorbax Sil, 9.4×25 cm column) using ethyl acetate-hexane mixtures. The first compound to elute was the (S)-(−)-p-tolyl-(2R)-2,3-dimethylbutylsulfoxide (3) and the second compound was the (S)-(−)-p-tolyl-(2S)-2,3-dimethylbutyl sulfoxide (4) MS m/z (relative intensity 224 ($M^+$, 6), 208 (14), 140 (100), 139 (8), 124 (30), 92 (22), 91 (21), 44 (10), 43 (71), 28 (34), 27 (25); $^1H$ NMR ($CDCl_3$) 6 0.80 (3H, d, J=7.0 Hz), 0.89 (3H, d, J=7.0 Hz), 0.98 (3H, d, J=6.5 Hz), 1.6-1.82 (2H, m), 2.42 (3H, s, $CH_3$—Ar), 2.71 (2H, m), 7.34 (2H, d, J=15 Hz) (H-aryl ortho), 7.54 (2H, d, J=15 Hz, H-aryl ortho). (2S) sulfoxide 4 $[\alpha]_D^{20}=153.5$ (c=4 in $CHCl_3$); (2R) sulfoxide 3 sulfoxide $[\alpha]_D^{20}=-444.8$ (c=4 in $CHCl_3$).

EXAMPLE 2

(2S)-2,3-Dimethylbutyl-p-tolylsulfone (6)

(2S)-2,3-Dimethylbutyl-p-tolylsulfoxide (4) (52 mg, 0.2 mmol) was dissolved in 1.0 mL of anhydrous dichloromethane and 60 mg (0.3 mmol) of 3-chloroperoxybenzoic acid (80–85%, Sigma) added with stirring. The reaction mixture was stirred for 2 h and quenched with 10% sodium bicarbonate. More dichloromethane was added and the combined organic extracts were washed with aqueous sodium sulfite and brine and dried with $MgSO_4$. The solvent was removed in vacuo and the crude sulfone was purified by silica gel flash chromatography using hexane ethyl acetate mixtures to afford sulfone (6) as a colorless oil. For analytical purposes this was also purified by HPLC (Zorbax Sil 9.4×25 cm column) using 10% ethyl acetate in hexane to give 42 mg of pure (2S)-sulfone (6): $[\alpha]_D^{20}=+17$ (c=3.5 in $CHCl_3$); MS m/z (relative intensity) 240 ($M^+$, 3), 197 (5), 157 (100), 92 (19), 91 (27), 85 (25), 84 (31), 43 (72); $^1H$ NMR δ 0.77 (3H, d, J=7 Hz), 0.82 (3H, d, J=7.0 Hz), 1.00 (3H, d, J=7.0 Hz), 1.66-1.98 (2H, m), 2.45 (3H, s, $CH_3$-Aryl), 2.86 (1H, dd, J=8, 11 Hz), 3.06 (1H, dd, j=4, 12 Hz), 7.35 (2H, d, J=7.0 Hz, H-aryl ortho), 7.75 (2H, d, J=8, H-aryl ortho).

EXAMPLE 3

(2R)-2,3-Dimethylbutyl-p-tolylsulfone (5)

The (2R)-sulfone (5) was prepared by oxidation of sulfoxide 3, using the experimental procedure as described in Example 2 above. The resulting (2R) sulfone (5) showed an optical rotation of $[\alpha]_D^{20}=-19$ (c-1.4, $CHCl_3$).

EXAMPLE 4

1α-Hydroxy-24-epi-vitamin $D_2$ (10)

To a stirred solution of 30 mg (125 μmol) of (2S)-2,3-dimethylbutyl-p-tolylsulfone (6) in 300 μL anhydrous tetrahydrofurane (containing 1.10-phenanthroline as an indicator) was added under argon at −78° C. 18 μL (130 μmol) of diisopropylamine followed by 86 μL of a solution of n-BuLi in hexane (1.50M, 130 μmol). The solution was stirred at −78° C. for 15 min (dark brown color), and 4 mg (7 μmol) of the protected aldehyde (7, $X^1=X^2=$t-BuMe$_2$Si) in 0.3 mL of anhydrous tetrahydrofurane was added and the mixture stirred under argon at −78° C. for 1 h. The reaction mixture was quenched with 1 mL of saturated $NH_4Cl$ solution, warmed to 0° C. and extracted with ethyl acetate, and the organic phase was washed with saturated NaCl. The organic phase was dried with $MgSO_4$, filtered and evaporated. The residue was redissolved in ethyl acetate, passed through a Sep Pak column in ethylacetate and evaporated. The residue was purified by HPLC (Zorbax Sil 9.4×25 cm column) using 10% ethylacetate in hexane to give 3.3 mg (58%) of the hydroxysulfones (8, $X^1=X^2=$t-BuMe Si). MS m/z (relative intensity) 8.2 ($M^+$, 20), 680 (34), 440 (52), 248 (64), 157 (65), 75 (100).

A saturated solution of $Na_2HPO_4$ in methanol (1.0 mL) was added to a stirred solution of the 3.3 mg sulfone (8) in 1.0 mL of anhydrous tetrahydrofuran followed by 160 mg of powdered anhydrous $Na_2HPO_4$. The mixture was stirred under argon for 15 min, cooled to 0° C. and fresh 5% sodium amalgam (ca. 400 mg) added. The mixture was stirred at 5° C. for 20 h; 5 mL of hexane added and the hexane layer decanted. The solid material was then extracted with 10% ethyl acetate in hexane (3×5 mL). The combined organic phase was washed with saturated NaCl and filtered through a Sep Pak cartridge and evaporated. Final purification on HPLC (Zorbax Sil 9.4×25 cm column) (10% ethyl acetate in hexane as solvent) gave 1.05 mg (40%) of vitamin $D_2$ derivative (9, $X^1=X^2=$t-BuMe$_2$Si). (As a byproduct, 0.47 mg of the 22-hydroxylated derivative was also obtained.) MS m/z (relative intensity) 640 ($M^+$, 24), 508 (65), 248 (67), 147 (13), 73 (100), 69 (58); $^1H$ NMR δ0.54 (3H, s, 18-$CH_3$), 4.19 (1H, m, 3-H), 4.35 (1H, m, 1-H), 4.86 (1H, S, 19Z-H), 5.17 (3H, m, 19E-H and 22-23-H-S), 6.00 (1H, d, J=9.6 Hz, 7-H), 6.23 (1H, d, J=8.8 Hz, 6-H). The hydroxy-protected diol (9, 800

μg) was dissolved in 0.5 mL of anhydrous tetrahydrofuran, and to this solution was added 90 μL 1M solution of tetrabutylammonium fluoride in tetrahydrofuran. The mixture was stirred under argon at 55° C. for 1 h. The mixture was cooled and 5 mL of ether added. The organic phase was washed with saturated NaCl solution and dried over anhydrous MgSO$_4$, evaporated and redissolved in 20% 2-propanol in hexane and filtered through Sep-Pak. Preparative HPLC (Zorbax-Sil 9.4 mm x 25 cm column) in 20% 2-propanol in hexane gave 308 pg 1μ-hydroxy-24-epi-vitamin D$_2$ (10, $X^1=X^2=H$) 1α-Hydroxy-24-epi-vitamin D$_2$ exhibited the following spectral properties: UV (EtOH) $\lambda_{max}$: 264 nm, $\lambda_{min}$ 228; MS m/z (relative intensity) 412 (M$^+$, 13), 394 (21), 376 (7), 287 (4), 269 (7), 251 (6), 252 (31), 251 (6), 152 (35), 151 (15), 134 (100), 69 (50), 55 (73); δ0.49 (3-H, S, 18-CH$_3$), 0.77 (3-H, d, J=7.1 26 or 27-CH$_3$), 0.85 (3H, d, J=6.8, 28-CH3), 0.94 (3H, d, J=6.5, 21-CH$_3$), 4.94 (1H, S, 19Z-H), 5.13 (2H, m, 22 and 23 H) (5.11, 5.13, 5.14), 5.26 (1H, S, 19E-H), 5.99 (1H, d, J=11.2 Hz, 7-H), 6.35 (1H, d, J=11.2 Hz, 6-H), 4.21 (1H, m, 3-H), 4.41 (1H, m, 1-H). 1α-Hydroxy-24-epi-vitamin D$_2$ can be distinguished from the previously known 1α-hydroxyvitamin D$_2$ by reverse phase HPLC (4.6 mm×25 cm, ODS-Zorbax column) with 15% water in acetonitrile. The first compound to elute in this system was 1α-hydroxy-24-epi-vitamin D$_2$ and the second, the known Biological Activity of 1α-Hydroxy-24-epi-vitamin D$_2$ The new analogue was tested in the vitamin D-deficient rat. These tests indicate that lo-hydroxy-24-epi-vitamin D$_2$ has a biological activity spectrum that is distinctly different from that of the previously known 1α-hydroxyvitamin D$_2$. In Table 1 below, representative assay results are given. These include tests of intestinal calcium transport activity ("S/M ratios"), and of bone mineral mobilization as reflected by serum calcium levels. These assays were conducted according to standard procedures (see e.g., U.S. Pat. No. 4,588,716). The rats used in these assays were made vitamin D-deficient by maintenance on a vitamin D-free, low calcium diet (0.02% Ca, 0 37% P) for 3½ weeks. They received the test compounds (or vehicle alone; -D control group) 20 h prior to sacrifice.

The data of Table 1 show that the new analogue, 1α-hydroxy-24-epi-vitamin D$_2$ exhibits high activity in stimulating intestinal calcium transport being essentially equivalent in this activity to the known 1α-hydroxyvitamin D$_2$. In contrast, the new compound exhibits no activity in mobilizing calcium from bone. Thus the new compound, although structurally closely related to the known 1α-hydroxyvitamin D$_2$, exhibits a remarkably different activity profile. In stimulating the absorption of calcium, but not its liberation from home, the new analogue is highly suitable as a therapeutic agent for the prevention or treatment of physiological conditions characterized by the loss of bone mass.

TABLE 1

Intestinal Calcium Transport and Bone Mobilization Activity of 1α-Hydroxyvitamin D$_2$ and 1α-Hydroxy-24-Epi-Vitamin D$_2$

| | Amount (pmol) | Ca Transport S/M Ratio | Bone Mobilization Serum Ca, mg % |
|---|---|---|---|
| D (Control) | 0 | 2.5 ± 0.35 | 3.7 ± 0.20 |
| 1α-Hydroxy-24-epi-vitamin D$_2$ | 325 | 4.3 ± 0.42$^a$ | 3.9 ± 0.39$^b$ |
|  | 650 | 4.4 ± 0.70$^a$ | 4.1 ± 0.23$^b$ |
| 1α-Hydroxy-vitamin D$_2$ | 325 | 5.4 ± 0.37$^a$ | 5.3 ± 0.15$^a$ |

TABLE 1-continued

Intestinal Calcium Transport and Bone Mobilization Activity of 1α-Hydroxyvitamin D$_2$ and 1α-Hydroxy-24-Epi-Vitamin D$_2$

| | Amount (pmol) | Ca Transport S/M Ratio | Bone Mobilization Serum Ca, mg % |
|---|---|---|---|

$^a$Significant difference compared to respective control groups, p < 0.001.
$^b$no significant difference compared to control.

The results of Table 1 demonstrate that, in terms of its calcemic action, the novel 1α-hydroxy-24-epi-vitamin D$_2$ exhibits a biological activity spectrum similar to that of the known 1α,25-dihydroxy-24-epi-vitamin D$_2$. However, further tests showed that the new compound is quite different from the known 24-epi-D$_2$ derivative in its activity in inducing the differentiation of malignant cells to normal monocytemacrophages. Differentiation activity was assayed using human leukemia cells (HL-60 cells), according to two standard tests, namely the nitroblue tetrazolium reduction (NBT-reduction) and the phagocytosis assays, and as shown in Table 2, the new compound was compared against 1α,25-dihydroxyvitamin D$_3$ (a highly potent differentiation agent) and 1α,25-dihydroxy-24-epi-vitamin D$_2$.

The assays were conducted as described by Ostrem et al. (J. Biol. Chem. 262, 14164–14171, 1987), and by DeLuca et al. (U.S. Pat. No. 4,717,721). The results given in Table 2 demonstrate that 1α,25-dihydroxyvitamin D$_3$ standard has, as expected, remarkable HL-60 cell differentiation activity. Even at doses as low as $10^{-8}$M, this compound produced approximately 64–67% differentiation in the 4-day trial period in both the NBT-reduction and the phagocytosis assay. 1α,25-Dihydroxy-24-epi-vitamin D$_2$ is somewhat less active (about 5 times less active than 1α,25-dihydroxyvitamin D$_3$ standard), but also shows very potent activity in this system, e.g. better than 60% differentiation at $5\times10^{-8}$M and 80% differentiation at a concentration of $10^{-7}$M. In contrast, 1α-hydroxy-24-epi-vitamin D$_2$ possesses little or no cell differentiation activity. At best, only 16–20% differentiation was observed at a concentration of $10^{-7}$M, and at a concentration of $1-2\times10^{-8}$M, where the 1α,25-dihydroxy-24-epi-vitamin D$_2$ compound shows 40–50% differentiation, the new analogue does not elicit a significant differentiation response. Thus, 1α-hydroxy-24-epi-vitamin D$_2$ has little or no activity in promoting differentiation of promyelocytes to monocytes. These results show a marked biological difference between the present compound and the previously produced 1,25-dihydroxy-24-epi-vitamin D$_2$.

TABLE 2

Activity of 1α-Hydroxy-24-Epi-Vitamin D$_2$ in HL-60 Cell Differentiation

| Compound | Concentration (M) | % Differentiation NBT Reduction | Phagocytosis |
|---|---|---|---|
| 1α,25-Dihydroxy-vitamin D$_3$ | 1 × 10$^{-7}$ | 87 ± 2 | 89 ± 3 |
|  | 1 × 10$^{-8}$ | 64 ± 2 | 67 ± 3 |
| 1α,25-Dihydroxy-24-epi-vitamin D$_2$ | 1 × 10$^{-7}$ | 80 ± 3 | 81 ± 3 |
|  | 5 × 10$^{-8}$ | 64 ± 3 | 62 ± 3 |
|  | 2 × 10$^{-8}$ | 48 ± 3 | 49 ± 2 |
|  | 1 × 10$^{-8}$ | 39 ± 3 | 40 ± 3 |
| 1α-Hydroxy-24-epi-vitamin D$_2$ | 1 × 10$^{-7}$ | 22 ± 2 | 16 ± 2 |
|  | 5 × 10$^{-8}$ | 14 ± 2 | 9 ± 1 |
|  | 2 × 10$^{-8}$ | 6 ± 2 | 6 ± 3 |
|  | 1 × 10$^{-8}$ | 4 ± 2 | 4 ± 2 |

Thus the preceding assays demonstrates that the new 1α-hydroxy-24-epi-vitamin $D_2$ exhibits a distinct and unique spectrum of activities—namely high potency in stimulating calcium transport, no activity in mobilizing calcium from bone, and little, if any, differentiation activity—which clearly distinguishes the compound from those of the prior art.

The new compound, therefore, represents a valuable addition to the repertoire of useful therapeutic agents, and may be applied advantageously in situations where the specific stimulation of intestinal calcium transport is desired, e.g. diseases such as osteodystrophy or osteoporosis characterized by loss of bone mass.

For treatment purposes, the novel compound of this invention may be formulated as a solution in innocuous solvents, or as an emulsion, suspension or dispersion in suitable solvents or carriers, or as pills, tablets or capsules, together with solid carriers, according to conventional methods known in the art. The compound is advantageously administered by injection, or by intravenous infusion of suitable sterile solutions, or in form of liquid or solid doses via the alimentary canal. Doses of from 1 μg to 50 μg per day of 1α-hydroxy-24-epi-vitamin $D_2$ are appropriate for treatment purposes, such doses being adjusted according to the disease to be treated and the response of the subject as is well understood in the art. Since the new compound exhibits specificity of action, it is suitably administered alone, in situations where only calcium transport stimulation is desired, or together with graded doses of another active vitamin D compound—e.g. 1α-hydroxyvitamin $D_2$ or $D_3$, or 1α,25-dihydroxyvitamin $D_3$—in situations where some degree of bone mineral mobilization (together with calcium transport stimulation) is found to be advantageous.

What is claimed is:

1. A compound characterized by the structure:

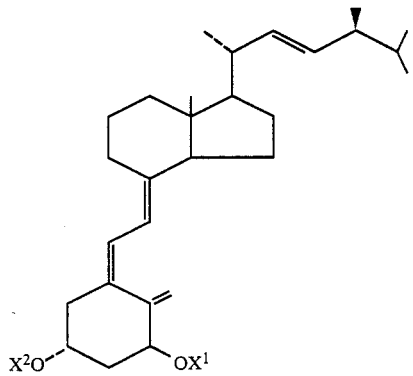

where $X^1$ and $X^2$ are selected from the group consisting of hydrogen, acyl and alkylsilyl.

2. The compound of claim 1 where $X^1$ and $X^2$ represent hydrogen.

3. A pharmaceutical composition containing an effective amount of a compound of claim 1 together with a pharmaceutically acceptable excipient.

4. A pharmaceutical composition containing an effective amount of the compound of claim 2 together with a pharmaceutically acceptable excipient.

5. The composition of claim 3 wherein the compound is present in an amount of from 1 μg to 50 μg.

6. The composition of claim 4 wherein the compound is present in an amount of from 1 μg to 50 μg.

7. 1α-hydroxy-24-epi-vitamin $D_2$.

* * * * *

UNITED STATES PATENT AND TRADEMARK OFFICE
CERTIFICATE OF CORRECTION

PATENT NO. : 4,973,584
DATED : November 27, 1990
INVENTOR(S) : Hector F. DeLuca et al It is certified that error appears in the above-indentified patent and that said Letters Patent is hereby corrected as shown below:

ON THE TITLE PAGE:

Add Item [73], Assignee: Wisconsin Alumni Research Foundation
Madison, Wisconsin Signed and Sealed this Twenty-fifth Day of February, 1997

Attest:

BRUCE LEHMAN

*Attesting Officer*    *Commissioner of Patents and Trademarks*